US011154564B2

(12) United States Patent
Mercati et al.

(10) Patent No.: US 11,154,564 B2
(45) Date of Patent: Oct. 26, 2021

(54) COMPOSITION FOR COUGH (71) Applicant: Aboca S.p.A. Società Agricola, Sansepolcro (IT)

(72) Inventors: Valentino Mercati, Sansepolcro (IT); Luisa Mattoli, Sansepolcro (IT); Paola Polenzani, Sansepolcro (IT)

(73) Assignee: ABOCA S.P.A. SOCIETÀ AGRICOLA, Sansepolcro (IT)

( * ) Notice: Subject to any disclaimer, the term of this patent is extended or adjusted under 35 U.S.C. 154(b) by 0 days.

(21) Appl. No.: 16/480,943

(22) PCT Filed: Feb. 12, 2018

(86) PCT No.: PCT/IB2018/050837
§ 371 (c)(1),
(2) Date: Jul. 25, 2019

(87) PCT Pub. No.: WO2018/150309
PCT Pub. Date: Aug. 23, 2018

(65) Prior Publication Data
US 2019/0388448 A1  Dec. 26, 2019

(30) Foreign Application Priority Data
Feb. 15, 2017  (IT) .................. 102017000016964

(51) Int. Cl.
| *A61K 36/00*   | (2006.01) |
| *A61K 31/7034* | (2006.01) |
| *A61K 9/19*    | (2006.01) |
| *A61K 31/715*  | (2006.01) |
| *A61K 35/644*  | (2015.01) |
| *A61K 36/185*  | (2006.01) |
| *A61K 36/61*   | (2006.01) |
| *A61K 36/68*   | (2006.01) |
| *A61K 36/73*   | (2006.01) |
| *A61K 36/752*  | (2006.01) |
| *A61K 47/26*   | (2006.01) |

(52) U.S. Cl.
CPC ........... *A61K 31/7034* (2013.01); *A61K 9/19* (2013.01); *A61K 31/715* (2013.01); *A61K 35/644* (2013.01); *A61K 36/185* (2013.01); *A61K 36/61* (2013.01); *A61K 36/68* (2013.01); *A61K 36/73* (2013.01); *A61K 36/752* (2013.01); *A61K 47/26* (2013.01)

(58) Field of Classification Search
None
See application file for complete search history.

(56) References Cited

U.S. PATENT DOCUMENTS

| 4,401,651 A      * | 8/1983  | Knutson ............... A61K 31/79 424/667 |
| 2002/0040050 A1  * | 4/2002  | Xu ......................... A61P 37/06 514/456 |
| 2013/0273113 A1  * | 10/2013 | Baker, Jr. ............... A61K 39/39 424/278.1 |

FOREIGN PATENT DOCUMENTS

| WO | WO-2006032091 A2 * | 3/2006 | ......... A61K 2300/00 |
| WO | WO-2010003472 A2   | 1/2010 | |
| WO | WO-2010052568 A1   | 5/2010 | |
| WO | WO-2015059683 A1   | 4/2015 | |
| WO | WO-2015097640 A1   | 7/2015 | |
| WO | WO-2018150309 A1   | 8/2018 | |

OTHER PUBLICATIONS

International Search Report and Written Opinion for Application No. PCT/IB2018/050837, dated Mar. 29, 2018, European Patent Office, Netherlands, 10 pages.

* cited by examiner

*Primary Examiner* — Qiuwen Mi
(74) *Attorney, Agent, or Firm* — Sterne, Kessler, Goldstein & Fox P.L.L.C.

(57) ABSTRACT

The present invention relates to a new composition for use in the treatment of cough comprising one or more polysaccharide fractions of plantain, one or more polysaccharide fractions of marshmallow, honey, brown sugar, one or more polyphenolic fractions of agrimony comprising tannins.

8 Claims, 4 Drawing Sheets

COMPOSITION FOR COUGH

DESCRIPTION

The present invention relates to a new composition for use in the treatment of cough, comprising one or more polysaccharide fractions of plantain, one or more polysaccharide fractions of marshmallow, honey, brown sugar, one or more polyphenolic fractions of agrimony comprising tannins.

STATE OF THE PRIOR ART

Classic pharmacological therapy is essentially based on cough suppression by chemical and pharmacological mechanisms. On the basis of their mechanism of action, anticough drugs can be classified into 3 categories:
  Mucolytics: increase mucus fluidity with mechanisms of depolymerization of mucoproteic complexes and of nucleic acids.
  Expectorants: increase bronchial secretions and indirectly reduce mucus viscosity
  Sedatives: inhibit the cough centre, eliminating the symptom.

The limitations of anticough drugs lie in their specificity of action and in their side effects: mucolytics only act in moist cough; sedatives are indicated in dry cough only, hindering its physiological action; expectorants have a scarcely rational mechanism of action, so much so that in actual fact they are not prescribed. Moreover, anticough drugs are scarcely adequate in pediatric age: in fact, mucolytics and central sedatives are contraindicated under age 2 years.

Therefore, a treatment of cough by non-irritating compositions, effective, stable and free from drugs such as, e.g., cortisone-based drugs or antibiotics, which can therefore be used without contraindications due to overdosage of such typologies of drugs and therefore also suitable for pediatric use, is of evident interest in the state of the art.

SUMMARY OF THE INVENTION

Therefore, the present invention relates to a formulation for the treatment of cough whose components are able to interact synergistically so as to intervene locally with mechanical-physical effects of its physio-pathogenetic mechanisms and having, jointly with a mucoadhesive effect of mucosal protection, also a powerful anti-oxidizing effect.

The formulation of the invention is able to act with a mainly mechanical effect:
I. on inflammation (which is the factor triggering the cough), by an indirect action carried out through the formation of a protective layer which, on the one hand prevents further contact with external irritating agents and preserves mucous membrane hydration, and on the other hand, thanks to the intervention of anti-oxidizing substances, mitigates the noxious effect of the free radicals produced by infections;
II. on mucus, making it more fluid and therefore more easily removable by physiological clearance mechanisms, by hydration thereof due to water-attracting hydrophilic substances.

Thus, the cough symptoms can be mitigated without nullifying its physiological role and promoting a restoration of normal conditions of mucus and mucous membrane.

The Authors of the present invention have made a composition having good mucoadhesive and barrier effect properties on the mucous membrane, jointly with anti-oxidizing properties comparable to those of vitamin C dosages commonly used in antitussive formulations stable over time, therefore not requiring the presence of the stabilizers commonly used for ascorbic acid stabilization.

The Authors have in fact made a composition in which a single ingredient, represented by agrimony (Agrimonia) is accountable both for the strong mucoadhesive properties of the formulation, and for its anti-oxidizing properties, such anti-oxidizing properties being comparable to those of vitamin C, but being much more stable than said vitamin.

In fact, it is known that the rapid degradation of ascorbic acid in aqueous products is to date a highly relevant factor in the formulation of products containing it. It is also known that ascorbic acid oxidation occurs rapidly in an alkaline environment. Ascorbic acid degradation occurs both aerobically and anaerobically, and depends on many factors, such as oxygen, temperature, light, pH and storage conditions.

The composition subject-matter of the invention has instead shown excellent mucoadhesion and barrier effect abilities, anti-oxidizing activity comparable to that exerted by commonly used dosages of vitamin C, jointly with excellent stability over time. In fact, the composition of the invention, even in fluid form, proved stable when keeping the analyzed samples under extreme conditions, at 40° C. and 75% of relative humidity. Obtained data are reported in the stability assay, in the Examples section.

As expected from the literature, and as also observed by the Inventors, vitamin C proved to be markedly unstable in the same fluid form (with the same excipients).

The present invention therefore provides a composition optimized for the treatment of cough, whose components as selected exhibit barrier effect, mucoadhesive and anti-oxidixing effect jointly with excellent stability over time.

Therefore, the present invention relates to a composition for use in the treatment of cough comprising one or more polysaccharide fractions of plantain, one or more polysaccharide fractions of marshmallow, one or more polyphenolic fractions of agrimony comprising tannins, brown sugar, honey.

The present invention also relates to a process for the preparation of said composition in one or more polysaccharide fractions of plantain, one or more polysaccharide fractions of marshmallow, one or more polyphenolic fractions of Agrimony comprising tannins are mixed with honey, brown sugar and one or more pharmaceutically acceptable carriers and/or excipients.

GLOSSARY

For the purposes of the present invention, by "Plantain" it is meant *Plantago lanceolate*, by "Agrimony" *Agrimonia eupatoria* and by "Marshmallow" *Althaea officinalis* are meant.

By tops, or flowering tops, it is meant the term as commonly used in herbal medicine and in botanical treatises, therefore the aerial ends of the plant which contain leaves, stems (meant as branches and not as main stalk of the plant) and flowers, or at least one of these components.

By polysaccharide fractions of marshmallow and of plantain, there are meant fractions of extracts, preferably hydroalcoholic or aqueous ones, of marshmallow roots, and fractions of extracts, hydroalcoholic or aqueous ones, of plantain leaves, comprising polysaccharides.

By polyphenolic fractions of agrimony comprising tannins, there are meant fractions of extracts, preferably hydroalcoholic or aqueous ones, of tops or flowering tops of agrimony, comprising polyphenols, in particular comprising the polyphenolic subclass of tannins.

DETAILED DESCRIPTION OF THE FIGURES

FIG. 1 shows such percentage for a formulation according to the invention in the form of syrup with the following dilutions: non-diluted, diluted 1:2 and diluted 1:5.

FIG. 2 shows the resistance of the mucoadhesive layer obtained with the product in the form of syrup diluted 1:2 at different times, 0.5 h, 1 h and 2 h towards a simulated salivary solution (0.9% NaCl physiological solution).

DETAILED DESCRIPTION OF THE INVENTION

Cough is a sudden expiratory manoeuvre that can occur as a reflex or as a voluntary action and has the aim of freeing the respiratory tract from any material present (expectorate), thereby performing a role indispensable to the physiological functioning of the respiratory system.

However, this system for defending the respiratory tract becomes a pathological condition when protracting in time, owing to repeated irritative stimuli (infective agents, irritating substances) causing excessive production of secretions and mucus, which accumulate in the respiratory tract and become a concomitant cause of tussive stimulus.

The mucous membrane lining the respiratory tract plays a protective role of functional barrier between the external environment and the tissues:

a) represents a real physical barrier, protecting underlying tissues from contact with the outside;

b) due to the presence of ciliated cells, with synchronized and unidirectional movements pushes mucus-entrapped foreign matter toward the esophagus;

c) produces secretions and mucus;

d) performs immunological functions, and in the presence of a virus enacts a series of effective defense mechanisms crucial in the antiviral response.

Part of its protective function is performed by the mucus covering it, which is an adhesive, viscoelastic gel produced by goblet cells and whose main macromolecules are glycoproteins.

It should be taken into account that the mucus, which under normal conditions has a protective role, in case of infection or other type of irritation becomes itself cause of cough: in fact, an overproduction and a higher viscosity thereof are witnessed.

The main mechanisms which onset from an infective and/or irritative event causing phlogosis of ear and throat can be described as follows:

1. direct involvement of larynx and trachea, due to their nearness and to the close communication relationships with mouth, pharynx and nose;

2. transport of inflammation mediators produced in the infection site, through the bloodstream, to the lower respiratory tract, where they initiate an inflammatory response; studies on guinea pigs and humans demonstrated that chemical-type sensory stimuli afferent from nose or esophagus can increase sensitivity to cough of the central nerve pathways, contributing to the "hypertussive" state accompanying inflammatory diseases of the respiratory tract, nose and esophagus.

3. in the post-nasal drip a continuous presence of mucus occurs, often in the form of viscous filaments difficult to expel from the nasopharynx, which by descending along the pharynx irritates it. This irritation causes a loss of coordination between nerves and muscles of trachea and esophagus, so that part of excess secretions pour into the larynx, causing a mechanical stimulation thereof which translates into a persistent, continuous and irritating cough, very frequent in children An important role in cough mechanisms is performed by the different types of receptors localized at the esophagus level, whose stimulation can trigger cough by various mechanisms:

stimulation of tension mechanosensors by means of the repeated attempts at deglutition of the copious and viscous mucus in case of infective events;

stimulation of mucosal receptors sensitive to light pressure stimuli exerted by mucous filaments stagnating between hypopharynx and esophagus;

stimulation of nociceptors by inflammation mediators produced locally and carried by mucus to other sites (alike stimulation mechanisms have been demonstrated in guinea pig, even with acidic chemical stimuli)

On the basis of the fact that both the physiological mechanisms for protection of respiratory tract mucous membranes and the pathogenetic processes of cough are actually based on mechanical-type mechanisms (mucus and intact mucous membrane on the one hand, mucus overproduction and mechanical stimulation on the other hand) the Inventors deemed that intervening with an action of mucous membrane protection could be the only approach really effective.

The Inventors moreover sought and singled out a formulation, stable over time, based on substances of natural origins, that would have a high mucoadhesive ability, an effective barrier effect against irritating agents, jointly with a high anti-oxidizing action.

This required the development of a formulation that be active in its complexity, i.e. that its components be able to interact synergistically so as to intervene locally with mechanico-physical effects on its physio-pathogenetic mechanisms and concomitantly provide an anti-oxidizing effect enabling an effective protection from free radicals.

Bearing in mind such aim, a composition was made for use in the treatment of cough, comprising one or more polysaccharide fractions of plantain, one or more polysaccharide fractions of marshmallow, one or more polyphenolic fractions of agrimony comprising tannins, brown sugar and honey, along with one or more pharmaceutically acceptable carriers and/or excipients.

As indicated above, by polysaccharide fractions of plant x or y, or polyphenolic fractions of plant z comprising tannins, there are meant fractions of extracts of said plants, comprising the classes of compounds indicated and free from other classes of compounds commonly present in the parts of interest of the plant. In particular, the aforesaid fractions could be produced by hydroalcoholic extraction or aqueous extraction techniques. These fractions could be in form of hydroalcoholic or aqueous extracts, dry extracts, extracts dried by spray-drying technique (different from lyophilization), soft extracts or mixtures thereof.

The lyophilized extracts or the extracts dried by spray drying technique according to the invention can be lyophilized or dried hydroalcoholic or aqueous extracts. According to the invention, the aforesaid fractions are preferably standardized for content of characteristic markers.

In one embodiment, the polysaccharide fraction of plantain is a fraction (or a set of fractions) comprising polysaccharides having a molecular weight higher than 20000 Daltons at a percentage in weight greater than or equal to 3%. E.g., 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%. According to a further embodiment, the polysaccharide fraction of marshmallow is a fraction (or a set of fractions) comprising polysaccharides having a molecular weight higher than 20000 Daltons at a percentage in weight greater than or equal to 5%. E.g., 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%.

According to one embodiment, the polysaccharide fraction of marshmallow is a mucilaginous fraction extracted from said plant.

According to still another embodiment, the polyphenolic fraction of agrimony is a polyphenolic fraction (or a set of fractions) (i.e., comprising polyphenols), comprising tannins, comprising polyphenols at a percentage in weight greater than or equal to 3%. E.g., 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%.

In one preferred embodiment, the composition comprises a polysaccharide fraction of plantain comprising polysaccharides with molecular weight higher than 20000 Daltons at a percentage in weight greater than or equal to 3%; a polysaccharide fraction of marshmallow is a fraction comprising polysaccharides with molecular weight higher than 20000 Daltons at a percentage in weight greater than or equal to 5%, and a polyphenolic fraction of agrimony comprising tannins, comprising polyphenols at a percentage in weight greater than or equal to 3%.

In the case of plantain and Marshmallow, lyophilized extracts or extracts dried by spray-drying are preferred, since for polysaccharide extraction solutions with a low percentage of alcohol or water are conventionally used, and such drying techniques are the best in order to give to the fractions the suitable characteristics for storage. The preparation of such types of fractions can be carried out with well-known methodologies, therefore no further indication is needed for a technician in the field to carry out the present invention. However, in the Examples section there are reported suitable methods, not limiting the invention, for the preparation of fractions suitable for the composition of the invention.

The composition according to the invention is suitable for use in adult, geriatric-age, gestating, teenage and pediatric-age patients. The preparation of the extracts, as already mentioned, could be carried out according to any technique known to a person skilled in the art, in a specific embodiment, said extracts could be lyophilized extracts.

The honey could be bee honey, honeydew honey or a mixture thereof, and could be used it also in a lyophilized form or in any form.

The formulation could then comprise formulative agents such as thickening agents, flavourings, and preservatives (preservative agents) of natural or synthetic origin or other technological adjuvants that the technician skilled in the field could select according to the state of the art. By mere way of example, juices (such as lemon juice or other fruits flavours (e.g., natural orange flavour, natural lemon flavour, natural peach flavour, natural myrtle flavour, natural blackberry flavour), thickening agents (such as xanthan gum, gum arabic) could be selected.

Therefore, the above-described composition could consist in one or more polysaccharide fractions of plantain, one or more polysaccharide fractions of marshmallow, one or more polyphenolic fractions of agrimony comprising tannins, brown sugar, honey, and suitable excipients, flavours, preservatives.

In one preferred embodiment of the invention, the sole active principles comprised in the composition will be represented by one or more polysaccharide fractions of plantain, one or more polysaccharide fractions of marshmallow, one or more polyphenolic fractions of agrimony comprising tannins, brown sugar, honey.

Therefore, the composition of the invention can also be defined as a composition consisting of one or more polysaccharide fractions of plantain, one or more polysaccharide fractions of marshmallow, one or more polyphenolic fractions of agrimony comprising tannins, brown sugar, honey and pharmaceutically acceptable carriers and/or excipients.

According to one embodiment, the composition of the invention could comprise 30-60% w/w of brown sugar; 20-50% w/w of honey; 0.1-2% w/w of polysaccharide fraction of plantain; 0.1-2% of polysaccharide fraction of marshmallow; 0.1-2% of polyphenolic fraction of agrimony comprising tannins and at least one of pharmaceutically acceptable carriers and/or excipients, q.s. to 100%.

Therefore, to weight percentages near to the upper end of the range of honey, there will correspond weight percentages near to the lower end of the range of brown sugar and vice versa, as the total sum of the parts in weight of the ingredients, including at least one pharmaceutically acceptable carrier and/or excipient is 100.

In the above-indicated ranges, the lower and upper ends, all values comprised between such ends, and all possible combinations of parts in weight of the ingredients falling within such intervals and whose sum be 100 are comprised. Hereinafter, non-limiting examples of possible embodiments according to the invention are provided.

According to one embodiment, the composition of the invention could comprise 30-50% w/w of brown sugar; 30-50% w/w of honey; 0.1-1% w/w of polysaccharide fraction of plantain; 0.1-1% of polysaccharide fraction of marshmallow; 0.4-2% polyphenolic fraction of agrimony comprising tannins, and at least one among pharmaceutically acceptable carriers and/or excipients, so as to have the overall amount reach 100% (that is, "q.s. to 100%").

According to another embodiment, the composition of the invention could comprise 35-55% w/w of brown sugar; 30-50% w/w of honey; 0.1-1% w/w of polysaccharide fraction of plantain; 0.1-5% polysaccharide fraction of marshmallow; 0.2-2% polyphenolic fraction of agrimony comprising tannins and at least one among pharmaceutically acceptable carriers and/or excipients, q.s. to 100%.

According to a further embodiment, the composition of the invention could comprise 40-60% w/w of brown sugar; 20-30% w/w of honey; 0.1-1% w/w of polysaccharide fraction of plantain; 0.1-5% polysaccharide fraction of marshmallow; 0.2-2% polyphenolic fraction of agrimony comprising tannins and at least one among pharmaceutically acceptable carriers and/or excipients, q.s. to 100%.

According to a still further embodiment, the composition of the invention could comprise 40-60% w/w of brown sugar; 20-30% w/w of honey; 0.1-1% w/w of polysaccharide fraction of plantain; 0.1-1.7% polysaccharide fraction of marshmallow; 0.2-1% polyphenolic fraction of agrimony comprising tannins and at least one among pharmaceutically acceptable carriers and/or excipients, q.s. to 100%.

According to yet another embodiment, the composition of the invention could comprise 40-60% w/w of brown sugar; 20-30% w/w of honey; 0.1-1% w/w of polysaccharide fraction of plantain; 0.1-1.6% polysaccharide fraction of marshmallow; 0.3-1% polyphenolic fraction of agrimony comprising tannins and at least one among pharmaceutically acceptable carriers and/or excipients, q.s. to 100%.

According to yet another embodiment, the composition of the invention could comprise 40-60% w/w of brown sugar; 20-30% w/w of honey; 0.2-1% w/w of polysaccharide fraction of plantain; 0.1-1.6% of polysaccharide fraction of marshmallow; 0.3-1% polyphenolic fraction of agrimony comprising tannins and at least one among pharmaceutically acceptable carriers and/or excipients, q.s. to 100%.

In all embodiments of the invention, the term "polysaccharide fraction" comprises also a set of fractions, as well as the term "polyphenolic fraction" also comprises a set of fractions, as long as the classes of above-indicated compounds are present, preferably in the concentrations indicated in the present description.

The compositions of the invention are therefore comprised of a set of functional substances having chemicophysical properties such as to perform overall a mucus-fluidifying effect and an effect of protecting the mucous membrane at the level of the application site represented by the upper respiratory tract.

As is apparent from the experiments reported in the present description, the composition according to the present invention has a percentage of mucoadhesion, when measured by assessment of the ability of the product, non-diluted or diluted to 1:5, to adhere to cells of the buccal mucous membrane in culture, inhibiting lectin binding with membrane proteins, of between 85 and 50%. Said ability is measured by treating cells of the buccal mucous membrane with the substance to be assayed (in this case with the composition of the invention) and then with biotinylated lectin, detecting with a suitable system (e.g. streptavidin peroxidase-o-phenylalanine) the lectin bound to said cells, comparing the amount of bound lectin in the sample treated with the composition of interest with respect to the amount of bound lectin in the control, in which cells are not treated with the composition of interest.

The decrease in the absorbency value is proportional to the ability of the product to adhere ("mucoadhere") to cells. The mucoadhesive ability is expressed as a percentage of inhibition of glycoprotein/lectin binding, and represents the percentage of mucosal sites occupied by the product according to the equation:

$$\text{Percentage of mucoadhesion of the product} = (1 - \text{abs sample}/\text{abs control}) \times 100$$

Where abs is for absorbency measured with a spectrophotometer at $\lambda = 450$ nm The product is applied after dilution, taking into account the fact that in real use, right after delivery, a mixing with the saliva present in the oropharyngeal cavity occurs.

Figure 1:
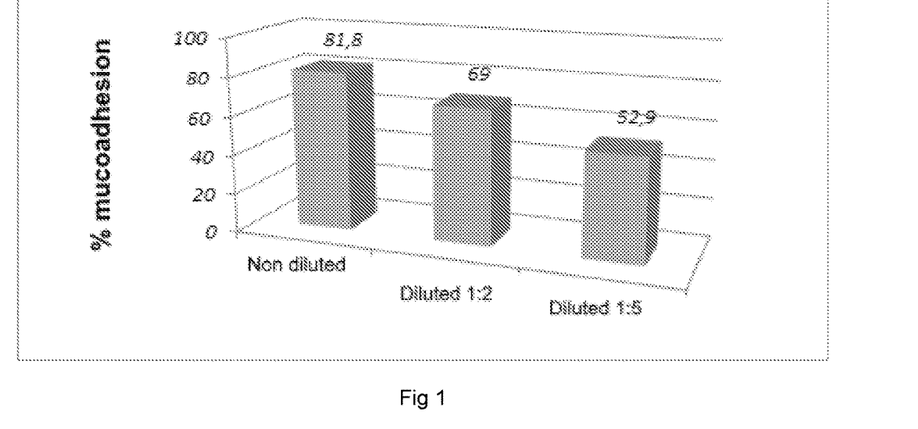
In FIG. 1, the mucoadhesivity percentage of the product under static conditions, at various dilutions, towards human buccal cells is reported, measured by assessment of the product ability to adhere to cells by inhibiting lectin binding with membrane glycoproteins, as illustrated in the detailed description and in the examples below.

According to the present invention, the composition, non-diluted or diluted to 1:5 with a suitable diluent, could have a percentage of mucoadhesion, measured with lectin binding assay, of between 85% and 50%, preferably between 82 and 52% (see FIG. 1).

With the expression of between 85% and 50% it is meant any integer, which could be 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50% and any decimal of the above-indicated integers lower than 85% and higher than 50% (therefore from 84.9% to 50.1%).

Any interval of mucoadhesive ability as measured above comprised between these two extremes is object of the invention.

Moreover, the composition of the invention has, as apparent from the assays carried out, a good resistance of the mucoadhesion to washing with saline, by subjecting the system to a 2 ml/min flow of artificial saliva on a Franz cell. This treatment, mimicking the resistance of the composition to saliva flow in situ, demonstrates that the composition of the invention is characterized by a high mucoadhesion lasting over time, as evident from the data reported in FIG. 2.

Moreover, the composition can be further or alternatively characterized in that it exerts a protective barrier effect, assessed by calculating the percentage of reduction of the production of a cytokine in experiments conducted on cells in the presence of the product of the invention with respect to a positive Control without product, following contact with a suitable inflammatory agent able to induce the production of said cytokine.

As measuring system, any known inflammatory agent and a corresponding cytokine activated thereby can be used. An example of possible inflammatory agent system is represented by lipopolysaccharide (LPS) and IL-6.

The barrier effect assay is a biological-type in vitro assay employed for assessing the ability of finished products and/or raw materials to protect, through the formation of a thin "insulating" layer, mucous membranes and skin from contact with environmental contaminants (dust, pollens, microorganisms, etc.)

The assay was developed to simulate in vitro the action exerted by products that are applied on skin and/or mucous membranes with the aim of creating a protective film against external aggressors.

The model takes advantage of the principle whereby cells subjected to contact with an inflammatory agent produce and secrete pro-inflammatory mediators (cytokines) in the extracellular environment in an amount related to the degree of inflammation caused; within a certain range, a direct proportionality exists between concentration and times of exposure to the inflammatory agent and amounts of cytokines released.

The experimental model adopted provides two chambers physically separated by a semi-permeable membrane (0.4 µm pores). Cells are seeded in the lower chamber, whereas the upper chamber accommodates the inflammatory agent; on the semi-permeable membrane separating the two chambers a thin film of the sample under analysis is stratified to highlight, if present, a barrier effect to the free transit of the inflammatory agent.

The semi-permeable membrane allows passage of the inflammatory agent in the lower chamber and constitutes the support on which the sample to be assayed is stratified. Depending on the "insulating" ability of the sample, a decrease of LPS migration from the upper chamber to the bottom one will be had (therefore a lesser stimulation of cells to cytokine production).

The assays carried out showed that the barrier effect exerted by the composition of the invention reduces IL-6 marker production, in cells subjected to the action of an inflammatory agent in the presence of said composition, of about the 65-75%, with respect to control cells subjected to the action of the same inflammatory agent in the absence of said composition.

This assay was developed in order to simulate in vitro the protective action of substances and formulations that, applied on skin and mucous membranes, form an "isolating" film towards external agents. The model takes advantage of the principle whereby cells subjected to contact with an inflammatory agent produce and secrete pro-inflammatory mediators (cytokines) in the extracellular environment in an amount related to the degree of inflammation caused. The assay envisages the setting up of two chambers physically separated by a semi-permeable membrane allowing transit of sufficiently small solutes.

In the lower chamber, consisting of a well containing plates for cell cultures, cells are grown (primary cell line of human fibroblasts—HUDE), whereas the upper chamber consists of the insert (transwell) and accommodates the inflammatory agent LPS.

On the internal surface of the transwell membrane separating the two chambers, a thin film of the sample being examined is stratified to assess any barrier effect (BE) upon free transit of the inflammatory agent.

The extent of the inflammatory reaction is assessed through semiquantitative dosage of the cytokines released in the culture medium of the lower chamber, in particular of interleukin 6 (IL-6) typical of the late phase of the inflammatory reaction.

Figure 3:
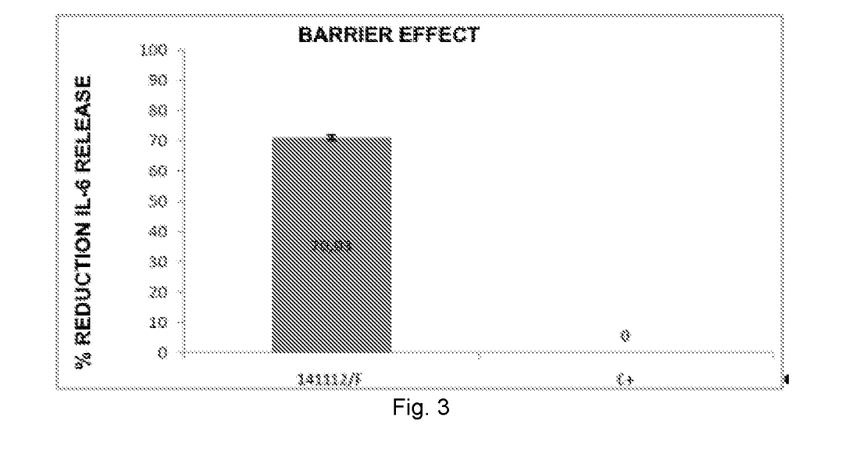
FIG. 3 shows the assessment of the barrier effect exerted by the product in syrup, which forms a protective film able to protect cells from inflammatory agents (LPS) insult.

In the Table below, the results obtained with the above-described experiment, summed up in FIG. 3 are reported.

| SAMPLE | IL-6 (pg/µL) | AVERAGE | S.D. |
| --- | --- | --- | --- |
| Composition according to Table 4 + LPS | 325.53 | 332.97 | 10.00 |
| Composition according to Table 4 + LPS | 344.33 | | |
| Composition according to Table 4 + LPS | 329.05 | | |
| Control + 1 (LPS) | 1274.47 | 1145.56 | 150.73 |
| Control + 2 (LPS) | 979.83 | | |
| Control + 3 (LPS) | 1182.39 | | |
| Control − 1 (MEM) | 72.03 | 63.28 | 8.82 |
| Control − 2 (MEM) | 54.40 | | |
| Control − 3 (MEM) | 63.41 | | |

From the results, it is apparent a remarkable reduction in concentration of IL-6 produced in experiments in which the assayed product is present.

The IL-6 value equal to 63.28 pg/µL detected for the Negative Control is comparable to a normal basal value, i.e. a non-inflammatory condition.

The next graph clearly shows the protection exerted by the products on the cells.

Data are expressed in terms of Fold Over (F.O.) compared to the Control C− by applying the following formula:

FOLD OVER (C−)=[measured IL-6]/[C−IL-6]

From the mean IL-6 values measured in the barrier assay and in the positive control, the percentage of IL-6 release reduction is calculated:

100−[(IL-6SAMPLE)/IL-6C+)×100]

Therefore, by applying the formula it is obtained a value of reduction of IL-6 production, in the experiments conducted in the presence of the assayed samples. The mean value obtained by performing the assay with the composition of the invention was of 70.93% compared to the positive control as reported in FIG. 3.

In order to verify to verify that the results depend on the sole barrier effect of the assayed samples and exclude any interferences with cytokine synthesis (anti-inflammatory effect), concomitantly to the barrier assay (B.A.) on each sample also an INTERNAL CONTROL (IC) assay was performed, in which the same steps of the above-described barrier assay were performed, inverting however the stressing order of the cells: cells were first stimulated with LPS and subsequently exposed to the sample.

Figure 4:
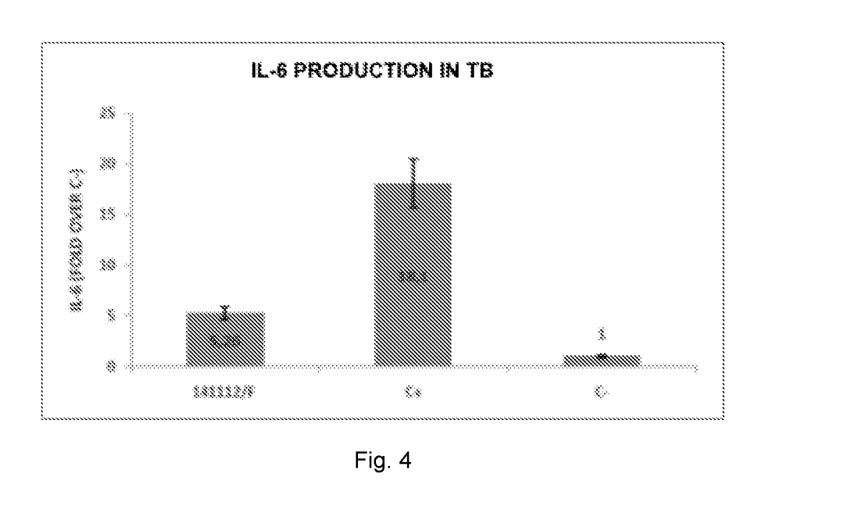
FIG. 4 shows data obtained by performing the same steps of the Barrier assay carried out for FIG. 3, inverting however the stressing order of the cells, i.e. first stimulating the cells with LPS, and subsequently exposing them to the sample (invention composition and positive control), the data obtained show that the anti-inflammatory activity of the composition of the invention is to be attributed to a barrier effect and that it is not a direct anti-inflammatory activity.

In this case, interleukin production is not affected by the presence of the samples, as shown by the graph reported in FIG. 4, indicating that the products do not possess direct anti-inflammatory activity. Lastly, the cell viability assay indicates that none of the operations carried out and of the treatments performed proved cytotoxic for the cells.

The results obtained, not reported, show a good ability by the tablets to form a protective barrier hindering the transit of the inflammatory agent LPS.

The authors of the invention have carried out experiments for assessing the anti-oxidizing activity of the composition of the invention at various dilutions by an experiment carried out in parallel on the composition of the invention with respect to a blank and with respect to vitamin C solubilized in said blank.

Therefore, the data reported hereinafter show how the composition of the invention also has an excellent anti-oxidizing activity, and how said composition remains stable also in fluid form with respect to the vitamin C suspended in the same excipients.

Figure 5:
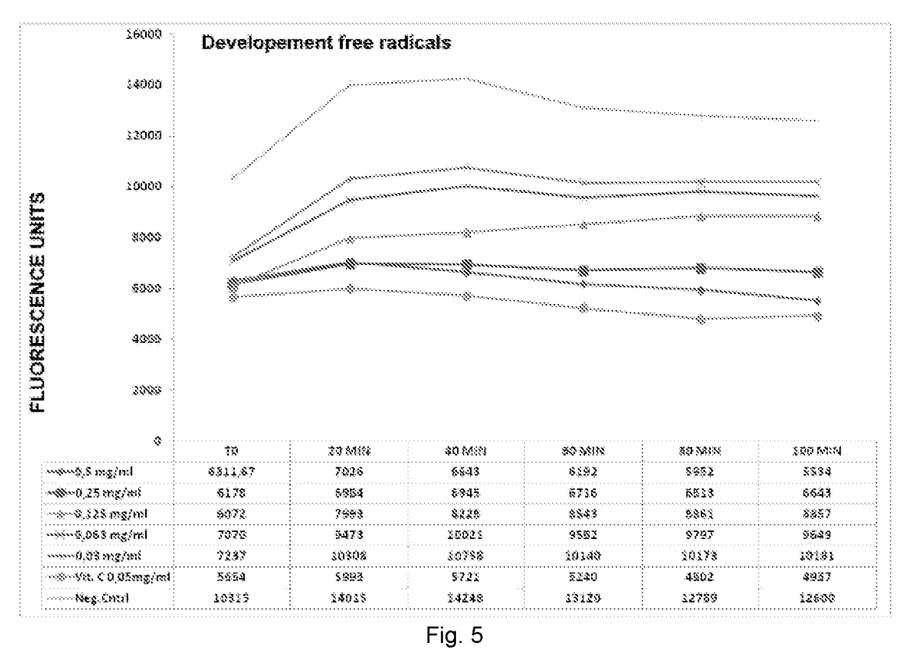
FIGS. 5 and 6 show the results, expressed respectively as graph representing the development of free radicals over time, and histogram representing the scavenger action over time of various concentrations of the composition. The experiments were performed on 1 gram of the composition of the invention, brought to a final volume of 10 ml in saline and assayed at the maximum concentration of 0.5 mg/ml and at the minimum concentration of 0.03 mg/ml of composition.
Figure 6:
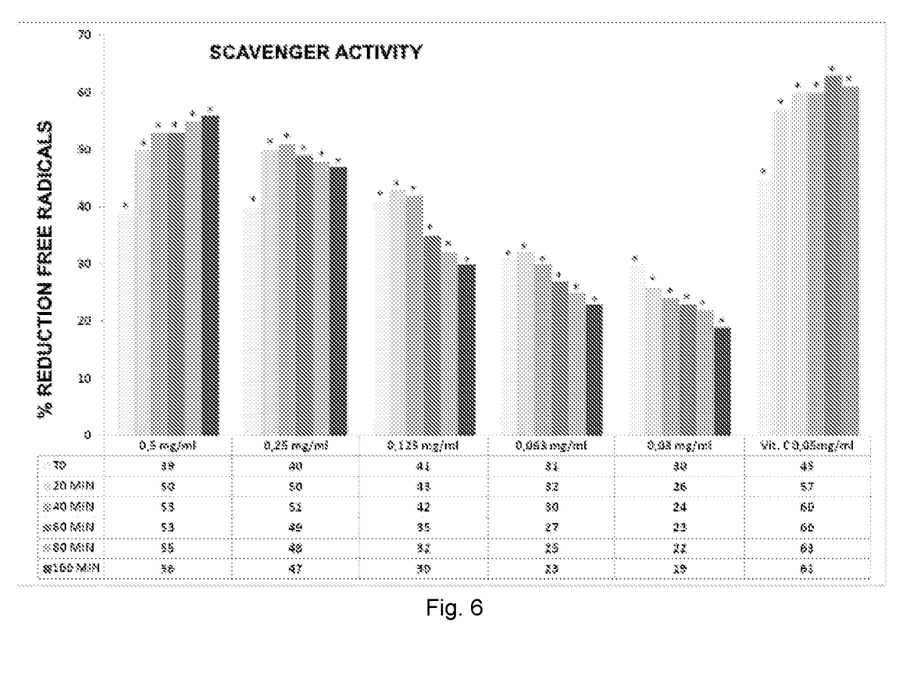
Figure 7:
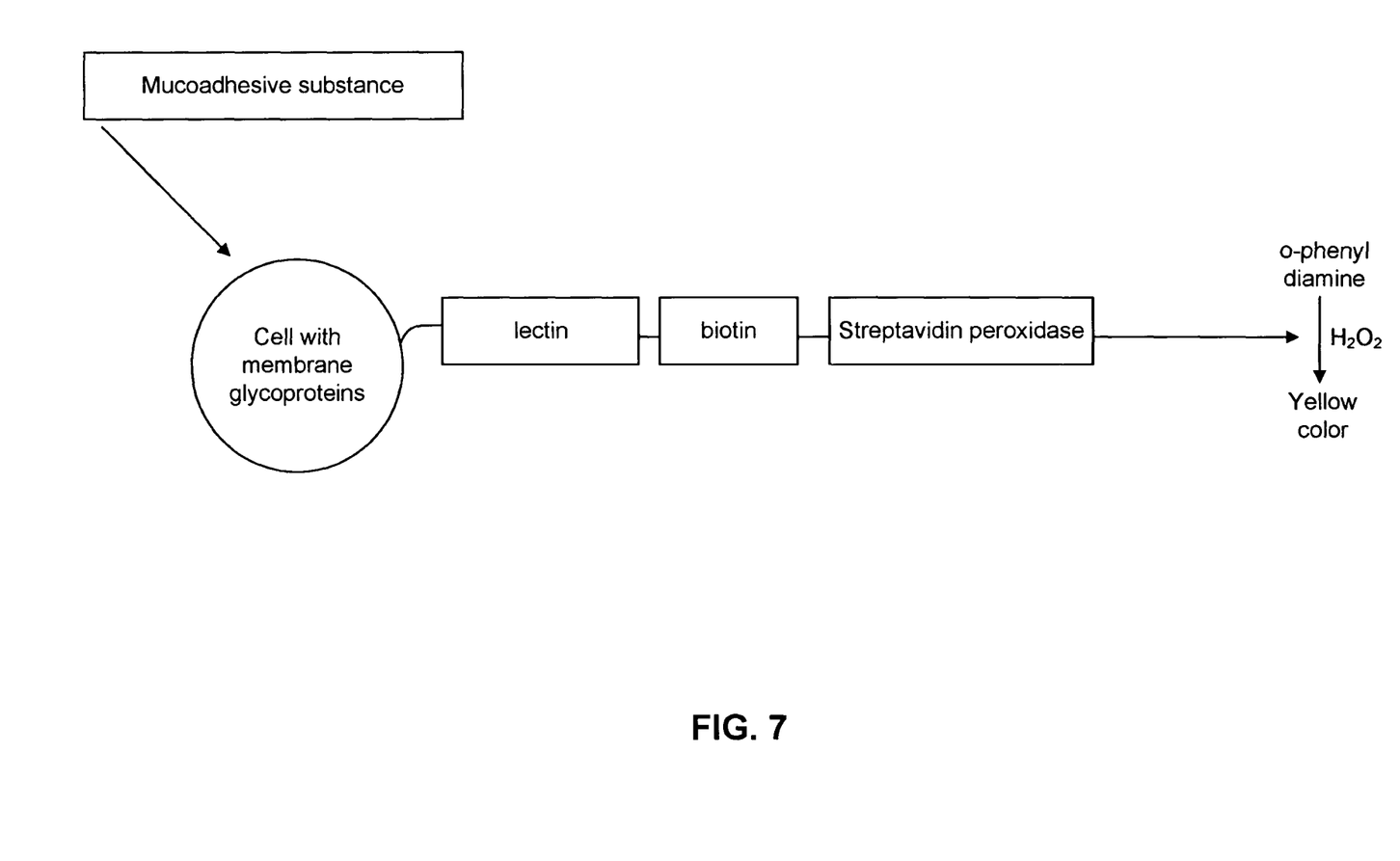
FIG. 7 shows the extent of mucoadhesion can be measured, e.g., by a colorimetric reaction enabling to quantify the sites on glycoproteins not engaged by the lectin, as engaged by the mucoadhesive product. The colorimetric reaction is possible thanks to a peculiar lectin labeling system.

The data obtained showed that the composition of the invention has a free radical scavenger action comparable to that exerted by vitamin C when introduced in replacement of the polyphenolic fraction of agrimony in the composition of the invention. FIGS. 5 and 6 show he results, expressed respectively as graph representing the development of free radicals over time and histogram representing the scavenger action over time of various concentrations of the composition. The experiments were performed on 1 gram of the composition of the invention, brought to a final volume of 10 ml in saline and assayed at the maximum concentration of 0.5 mg/ml and at the minimum concentration of 0.03 mg/ml of composition.

The experiment was carried out by assessing the effectiveness of the sample analyzed to neutralize the free radicals generated by treating cultured cells with a 500 µM $H_2O_2$ solution. The protection from $H_2O_2$-induced oxidative stress was expressed in terms of percentage of protection from development of free radicals measured with the assay reported in experimental example 2, at a time of 100 minutes.

In the experimental section there are reported in detail the experiments carried out for the assessment of the scavenger activity of the composition of the invention.

The experiments carried out showed that the composition of the invention has good scavenger action, able to neutralize $H_2O_2$-induced free radicals (FR): the first dose analyzed (0.5 mg/ml) reduces FR formation of the 39-50-53-53-55 and 56%, respectively, after each exposure time; the second dose analyzed (0.25 mg/ml) reduces FR formation of the 40-50-51-49-48 and 47%, respectively, after each exposure time; the third dose (0.125 mg/ml) reduces FR formation of the 41-43-42-35-32 and 30%, respectively after each exposure time; the fourth dose (0.0625 mg/ml) reduces FR formation of the 31-32-30-27-25 and 23%, respectively, after each exposure time, and the fifth dose (0.0313 mg/ml) significantly inhibits FR formation of the 30-26-24-23-22 and 19%, respectively, after each exposure time.

Ascorbic acid (0.05 mg/ml) has a scavenger action able to reduce FRs of the 45-57-60-60-63 e 61% respectively after the six times of exposure to the stress, therefore with values comparable to those of the first dose of composition examined.

According to the present invention, the composition can be made for oral administration and could be made in the form of tablet, pill, granules, powder, syrup, fluid, elixir, spray, suspension, emulsion, solution.

For oral administration the composition could be made in the form of daily unit dosages or of fractions of daily unit dosages (e.g., 2, 3, 4, 5, 6, or more tablets, pills, granule or powder single-doses, syrup, elixir, spray or fluid could be taken over the day, in accordance with the judgment of the treating doctor), and may contain conventional excipients including, e.g., binding agents, thickening agents, like gums (gum tragacanth, gum arabic), animal gelatine and polyvinylpyrrolidone; diluents, such as sugar, polyalcohols (sorbitol, mannitol, xylitol), maltodextrins, inorganic salts (bibasic calcium phosphate, calcium carbonate); disintegrants, like rice starch, corn starch and potato starch; lubricants, like magnesium stearate, polyethylene glycols with different molecular weights; glidants, like colloidal silica; antiadhering agents, such as, e.g., talc; wetting agents like sodium lauryl sulfate. The tablets may be coated according to methods well-known in standard pharmaceutical practice.

The composition could also be made in a liquid or semi-liquid form, as a suspension, emulsion, solution for oral administration, and could optionally contain natural flavourings giving a palatable taste thereto.

The composition in the form of powder or granule could be pre-metered in suitable containers and ready for use, either by ingestion as such or to be resuspended in an appropriate liquid such as water, tea, etc. In this case as well, the composition could contain natural flavourings giving a palatable taste thereto.

Evidently, all of the above-indicated excipients could be used in a pharmaceutically acceptable grade.

In one embodiment, the composition as described herein, in any one of the above-indicated embodiments, could be in the form of pharmaceutical composition, i.e. comprise pharmaceutical-grade ingredients, or it could be or be introduced into a medical food or into a medical device.

The composition according to the present description could be made in the form of pharmaceutical composition or of medical device according to any one of classes described in Directive 93/42/EEC on medical devices (comprising also substances and not only "devices" in the sense of objects).

In case of a syrup there could be used, besides the above-described active components and one or more of the previously described agents (preservatives, thickening agents, excipients, flavouring, etc.).

Therefore, in a specific embodiment of the present invention, the composition could be consisting of or comprise the following components:

TABLE 3

BROWN SUGAR
HONEY
EXCIPIENTS AND/OR CARRIERS
Polysaccharide fraction of marshmallow (e.g., lyophilized or spray-dried extract)
Polysaccharide fraction of plantain (e.g., lyophilized or spray dried extract)
Polyphenolic fraction of agrimony (e.g., lyophilized or spray-dried extract)
Optional CARRIERS, NATURAL FLAVOURINGS, EXCIPIENTS could be, e.g., in the following proportions:

TABLE 4

| General composition | % w/w |
|---|---|
| BROWN SUGAR | 40-60 |
| HONEY | 20-30 |
| WATER CARRIER | 10-40 |
| Polysaccharide fraction of plantain LEAVES | 0.1-1 |
| Polysaccharide fraction of MARSHMALLOW | 0.1-1 |
| Polyphenolic fraction of AGRIMONY | 0.1-1 |

The present invention also relates to a process for the preparation of said composition, wherein extracts of plantain, of marshmallow and of agrimony as described above are mixed with honey, brown sugar and one or more natural flavourings, preservatives, thickening agents and optionally with pharmaceutically acceptable excipients.

Lastly, the present invention also relates to a method for the treatment of dry cough, productive cough, URTI (upper respiratory tract infections)-associated cough and cough from post-nasal drip comprising the administration of a therapeutically active dosage of the composition of the invention to a patient in need thereof, wherein said patient can also be in pediatric age, geriatric age, gestating.

FORMULATION EXAMPLES

Hereinafter, some specific examples of liquid formulation are provided which are not to be understood as a limitation of the application.

TABLE 5

| COMPOSITION EXAMPLE 1 | % w/w |
|---|---|
| BROWN SUGAR | 30-50 |
| HONEY | 30-50 |
| DEIONIZED WATER and/or other suitable carrier or excipient | 40-60 |
| Polysaccharide fraction of plantain | 0.1-1 |
| Polysaccharide fraction of marshmallow | 0.1-1 |
| Polyphenolic fraction of agrimony | 0.4-2 |

TABLE 6

| COMPOSITION EXAMPLE 2 | % w/w |
|---|---|
| BROWN SUGAR | 35-55 |
| HONEY | 30-50 |
| SORBITOL SYRUP | 40-60 |
| Polysaccharide fraction of plantain LEAVES | 0.1-1 |
| Polysaccharide fraction of marshmallow | 0.1-1.5 |
| Polyphenolic fraction of AGRIMONY | 0.2-2 |

TABLE 6

| COMPOSITION EXAMPLE 3 | % w/w |
|---|---|
| BROWN SUGAR | 40-60 |
| HONEY | 20-30 |
| MANNITOL SYRUP excipient | 10-40 |
| Polysaccharide fraction of plantain LEAVES | 0.1-1 |
| Polysaccharide fraction of MARSHMALLOW | 0.1-1.5 |
| Polyphenolic fraction of AGRIMONY | 0.2-2 |

TABLE 7

| COMPOSITION EXAMPLE 4 | % w/w |
|---|---|
| BROWN SUGAR | 40-60 |
| HONEY | 20-30 |
| XYLITOL SYRUP excipient | 10-40 |
| Polysaccharide fraction of plantain LEAVES | 0.1-1 |
| Polysaccharide fraction of MARSHMALLOW | 0.1-1.7 |
| Polyphenolic fraction of AGRIMONY | 0.2-1 |

TABLE 8

| COMPOSITION EXAMPLE 5 | % w/w |
|---|---|
| BROWN SUGAR | 40-60 |
| HONEY | 20-30 |
| XYLITOL SYRUP excipient | 10-20 |
| MANNITOL SYRUP | 10-20 |
| Polysaccharide fraction of plantain LEAVES | 0.1-1 |
| Polysaccharide fraction of MARSHMALLOW | 0.1-1.6 |
| Polyphenolic fraction of AGRIMONY | 0.3-1 |

TABLE 9

| COMPOSITION EXAMPLE 6 | % w/w |
|---|---|
| BROWN SUGAR | 40-60 |
| HONEY | 20-30 |
| DEIONIZED WATER and/or other suitable carrier or excipient | 10-20 |
| GLUCOSE SYRUP | 10-20 |
| MALTITOL SYRUP | 10-20 |
| Polysaccharide fraction of PLANTAIN | 0.2-1 |
| Polysaccharide fraction of MARSHMALLOW | 0.1-1.6 |
| Polyphenolic fraction of AGRIMONY | 0.3-1 |

In one preferred embodiment, in all of the above-reported examples the polysaccharide and polyphenolic fractions are lyophilized or dried by spray drying.

EXPERIMENTAL EXAMPLES

The following experimental examples have the purpose of illustrating some of the assays performed on the composition of the present invention.

1. Mucoadhesion Assay

The mucoadhesive effect of a product, contributing to the formation of the protective film on the mucous membranes, can be assessed by suitable in vitro models.

The model used demonstrates that the mucoadhesivity of products intended for the treatment of the mucous membranes can be determined by assessment of percentage of lectin-glycoprotein binding inhibition. Mucosal buccal cells are initially treated with biotinylated lectin (Con-A), a protein contained in some Leguminosae (Canavalia ensiformis) having a high affinity for the glucoside and mannoside residues present in the glycoproteins of the membrane. The sites of the glycoproteins of the mucous membranes will thus be all engaged with the biotinylated lectin (treated with biotin, i.e. vitamin H). The cells, treated with biotinylated lectin, are charged with streptavidin peroxidase, making it possible to form the protein/glucose/lectin/biotin/streptavidin peroxidase complex thanks to the high affinity between biotin and streptavidin.

At this point, the cells are washed, and the protein/glucose/lectin/biotin/streptavidin peroxidase complex is quantified, assessing peroxidase activity, by means of a reaction of oxidation of the ortho-phenylenediamine (colorimetric assessment).

In fact, the protein/glucose/lectin/biotin/streptavidin peroxidase complex will catalyze the oxidation reaction:

The Intensity of the Yellow/Orange Coloration of the Solution (Measured Using a Spectrophotometer with λ=450 nm) is Proportional to the Quantity of Glycoprotein-Lectin Bonds and Therefore to the Quantity of Available Sites (Glycoproteins) for Mucoadhesion The absorbency value thus determined constitutes the "control".

When determining the mucoadhesivity of a product, the cells are treated preliminarily with this product (incubation at 30° C. for 15 minutes before the treatment with lectin).

If the product under examination contains mucoadhesive substances, these will bind to the glucoside and mannoside sites present in the membrane glycoproteins.

In the next phase, adding the sequence of biotinylated lectin, streptavidin peroxidase and ortho-phenylenediamine there will be obtained a less intense colouration, compared to the control, and this since part of the glucoside sites available for binding with the Con-A were already occupied by the mucoadhesive substances present in the product to be assayed. In fact, the initial binding between the mucoadhesive substances contained in the product to be assayed, and the glucoside sites partly compromises the subsequent conjugation of the Con-A with the streptavidin peroxidase complex and the consequent development of colour after addition of oxygenated water.

The decrease in the absorbency value is proportional to the ability of the substances under examination to "mucoadhere" to mucosal cells.

The mucoadhesive ability is expressed as a percentage of inhibition of glycoprotein/lectin binding, and represents the percentage of mucosal sites occupied by the product according to the expression:

Percentage of mucoadhesion of the product=(1−abs sample/abs control)×100

Furthermore, in addition to the mucoadhesive ability, it is also assessed the resistance of the mucoadhesive layer to the action of the salivary solution with which it comes to contact.

To this end, in a second phase of the experiment, the resistance over time (0.5-2 h) of the mucoadhesivity of the product after exposure to a continuous flow of artificial salivary solution.

To perform this assay, a system of Franz cells, generally being used in the assessment of percutaneous absorption of a substance or for the study of other processes of permeation through natural or artificial membranes.

Figure 2:
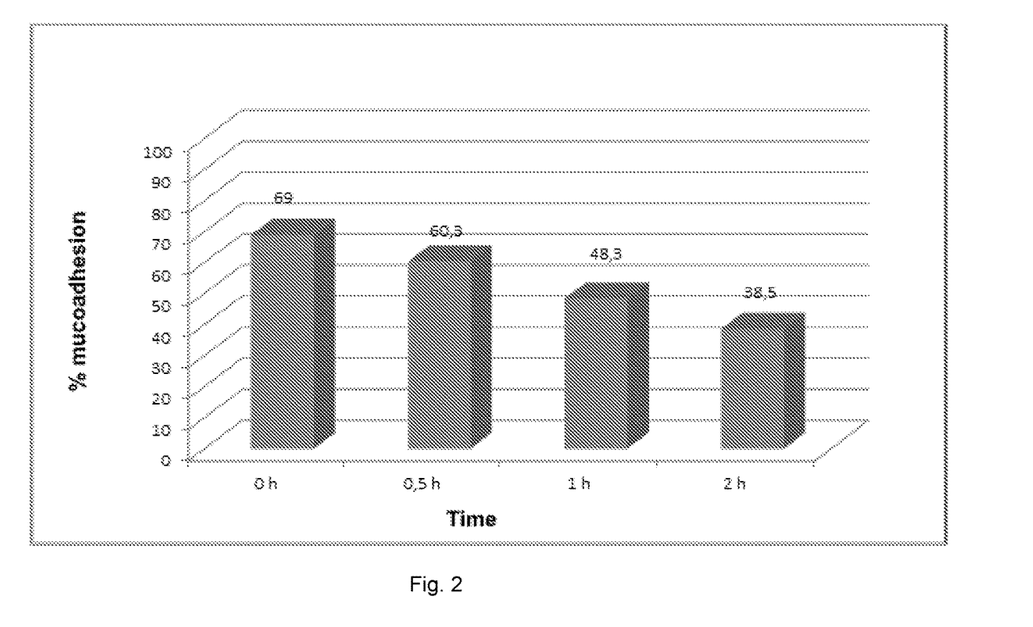
In FIG. 2, the resistance of the mucoadhesive layer under dynamic conditions is reported, i.e. assessing the product ability to remain adhered to the mucous membrane over time, by subjecting the system to a 2 ml/min flow of artificial saliva on a Franz cell as illustrated in the detailed description and in the examples below.

In the experiment, the buccal cellular cultures were deposed in the donor and were treated with formulations of the product as described in the assay at 2, at different dilutions, as reported in FIG. 2, (a dilution in all likelihood nearer to the real conditions that might occur in vivo). The donor was then fed with a continuous flow (2 ml/min.) of artificial salivary solution, by a peristaltic pump.

At the base of the donor, in the zone of separation with the receptor, a cellulose acetate membrane was placed, capable of allowing outflow of the salivary solution from the donor to the receptor, retaining the mucosal cells in the donor.

The salivary flow through the mucosal cells treated with the product under examination was regularly discontinued after 0.5, 1, 2 hours and the cells of the donor transferred into a suitable test tube for mucoadhesivity assessment.

In light of the results obtained, it is possible to state that the product, demostrating to possess good, resistant mucoadhesivity, can play an interesting protective role on mucosal cells of the oral tract.

In order to mimic the natural dilution of a syrup in the oral cavity, the mucoadhesivity assays were carried out on a product diluted 1:2; for greater completeness, also the mucoadhesivity of the product diluted 1:5 was assayed.

The mucoadhesivity percentage of the non-diluted, or diluted (1:2 and 1:5) product towards human buccal cells is reported in FIG. 1.

The resistance of the mucoadhesive layer obtained with the product diluted 1:2 at different times, 0.5 h, 1 h and 2 h towards a simulated salivary solution (0.9% NaCl physiological solution) is shown in FIG. 2.

2. Scavenger-Type Anti-Oxidizing Activity Assay

Assessment of anti-oxidizing activity of the sample on human cells exposed to chemical-type progressive oxidative stress.

The assessment of anti-oxidizing action is obtained from quantification of free radical formation in cells exposed to the sample and to oxidative stress.

The method applied is based on the use of the fluorimetric probe 2,7 dichlorofluorescein acetate—DCA-: this probe penetrates into cells, binds to cell membrane proteins and macromolecules. In this form, the probe is not fluorescent, only becoming fluorescent when oxidized by free radicals. Cells pretreated with DCA are exposed to the various dilutions of the sample and hydrogen peroxide. At regular intervals of 20 minutes to 100 minutes (5 measurements), free radical formation is assessed with a fluorimeter (Victor X4 Perkin Elmer): the scavenger action is obtained by a comparison of free radicals produced by cells exposed to the sample and to hydrogen peroxide and those exposed to the sole hydrogen peroxide.

Compositions according to examples 2, 4 and 6 were prepared.

1 g of composition consisting of 0.2% w/w of polysaccharide fraction of marshmallow, 0.35% of polysaccharide fraction of plantain, 0.2% of polyphenolic fraction of Agrimony comprising tannins, 25% of honey (for compositions 4 and 6, and 35% for composition 2), 46.6% of brown sugar and pharmaceutically acceptable carriers and excipients (according to the respective examples) was weighed and brought to a final volume of 10 ml (10 mg/ml) in saline. The assayed solution had a pH greater than 7. Starting from this mother solution, the first dilution was prepared at a concentration of 0.5 mg/ml in saline; therefrom, by applying a 1:2 dilution factor, the other four dilutions were obtained.

Other compositions according to the composition examples above were also assayed, giving analogous results. The absence of anti-oxidizing activity of the carriers and excipients used in the compositions was also verified. Concomitantly with the composition, also a positive control and an internal control were analyzed.

Positive Control: cells exposed to the 500 μM $H_2O_2$ solution.

Internal Control: cells exposed to an ascorbic acid solution (0.05 mg/ml).

Negative Control: cells exposed to the inoculation medium.

The assay was performed on a simple cell model consisting of a monolayer of stabilized human keratocytes (cells were purchased from IZSLER and are guaranteed as free from any viral/bacterial contamination and/or from mycoplasma).

Description of Reagents/Solutions and Related Abbreviations:

| | |
|---|---|
| Fetal Calf Serum | FCS |
| Sodium Dodecyl Sulfate | SDS |

Culture medium: Dulbecco High Glucose (D-MEM) completed with glutamine (2 mM), antibiotics such as penicillin (2000 UI/ml)-streptomycin (1000 UI/ml)-Fungizone (2 μg/ml) and Fetal Calf Serum (10%), hydrocortisone 0.5 ng/ml, Insulin 5 μg/ml, Epithelial Growth Factor 0.01 μg/ml

DMEM

Inoculation medium: Dulbecco High Glucose (D-MEM) completed with glutamine (2 mM), antibiotics such as penicillin (2000 UI/ml)-streptomycin (1000 UI/ml)-Fungizone (2 μg/ml) and Fetal Calf Serum (5%), hydrocortisone 0.5 ng/ml, Insulin

| | |
|---|---|
| 5 μg/ml, Epithelial Growth Factor 0.01 μg/ml | $DMEM_i$ |
| Phosphate buffer | PBS |

Neutral Red working solution: 0.4% stock solution is diluted in Minimum Essential Medium (MEM), filtered on paper immediately before use. Use concentration is 0.04% NRw Neutral red extraction fluid: prepared some minutes before use, consisting of 49%

| distilled water - 50% Ethanol - 1% glacial acetic acid | ExB |
| 2,7 DICHLOROFLUORESCEIN DIACETATE: 4 μm | DCA |

Dosages, Administration Route and Analytical Replicates

Two series (in the presence and absence of $H_2O_2$) of five base 2 dilutions of the sample: of 0.5-0.25-0.125-0.0625 and 0.0313 mg/ml, were set up. The same procedure was carried out to obtain the same five dilutions in a 500 μM $H_2O_2$ solution in saline. 150 μl per each dilution (in saline and in $H_2O_2$) were distributed into four wells on two different plates.

Day 1
Cell Seeding

Cultured cells were enzymatically detached from the growth medium and counted with an electronic cell counter (Scepter); a cell suspension was prepared (in inoculation medium) at the density of 300,000 cells/ml, which were then distributed into 96-well plates: 100 μl per well, obtaining a seeding density of 30,000 cells per well. Lastly, the plates were placed back to culture in an incubator at 37° C. and 5% $CO_2$-enriched humid atmosphere for the subsequent 24 hours.

Day 2
Exposure to DCA Probe

The inoculation medium was removed, cells were washed once with PBS, then PBS was discarded and 150 μl DCA (4 μM) was distributed in both plates. Then, the plates were placed back in incubator at 37° C. and 5% $CO_2$-enriched atmosphere for 15 minutes.

At the end of the DCA incubation period, the solution was removed, and cells were washed once with PBS, then 150 μl of the above-described dilutions of the sample and of the controls were distributed in the plates. Then, free radical formation was measured from T0 (right after inoculation into the two plates) every 20 minutes, up to 100 minutes (5 measurements) with a fluorimeter. At the end of the measurements, after the 100 minutes, the inoculate of both plates was removed and Neutral Red Uptake vitality assay was performed.

The cells were left contacting 150 μl of NRw for 3 hours at 37° C. in an incubator with 5% $CO_2$-enriched atmosphere. Neutral red (NR) penetrates the cells and is stored in lysosomes. Only vital cells that have kept membrane functionality intact will be able to retain NR. Accordingly, the greater the number of vital cells, the greater the amount of NR stored in the cells. At the end of the three hours of incubation, plates were collected, the NR solution was removed, and cells were subjected to washings with 150 μl of PBS to eliminate NR in excess. Then, extraction of Neutral Red accumulated in lysosomes was carried out by applying, in each well, 150 μl of ExB.

The extraction stage was protracted for 15 minutes under stirring at room temperature. Thus, a red fluid is obtained whose intensity, proportional to the number of vital cells present, is measured by spectrophotometric reading at 570±30 nm.

The intensity of emitted fluorescence and of Neutral Red extracted in 96-well plates was measured by fluorimetric and spectrophotometric reading at 540 nm with a Victor X4 (Perkin Elmer) plate reader.

Result Assessment and Calculation
Survival Rate Detection

% Vitality=[(O.D. Sample±$H_2O_2$/O.D. ControlPos/Neg)×100]

% Vitality inhibition=(100-% Vitality)

O.D.: optical density

O.D. Sample±$H_2O_2$: optical density average, obtained from cells exposed to the sample with and without $H_2O_2$ O.D. positive/Negative control: optical density media obtained from cells exposed to the $H_2O_2$ solution or to the sole saline (100% Vitality)

Assessment of Scavenger Anti-Oxidizing Activity

F.U.: fluorescence unit

F.U. positive control: average of F.U. emitted from cells exposed to the $H_2O_2$ solution (maximum production of free radicals)

F.U. negative control: average of F.U. emitted from cells not exposed to oxidative stress At each time interval of exposure (T0-T1-T2-T3-T4-T5) there were carried out:

1) Normalization the average of F.U. emitted from cells exposed to the sample, to vitamin C without oxidative stress, is subtracted from the average of F.U. emitted from cells exposed to the sample, to vitamin C and oxidative stress. In other words, the average values of fluorescence emitted from the non-stressed plate were subtracted from the average values of fluorescence emitted from the stressed plate.

2) Calculation of the Percentage of Free Radical Abatement:

% FR inhibition=[100−(F.U. Sample$_{pos}$−F.U. Sample$_{neg}$)/(U.F.Control$_{pos}$−U.F.Control$_{neg}$)*100]

F.U. Sample$_{pos}$: cells exposed to the sample and to oxidative stress

F.U. Sample$_{neg}$: cells exposed to the sole sample

F.U. Control$_{pos}$: cells exposed to the sole oxidative stress

F.U. Control$_{neg}$: cells exposed to saline without oxidative stress

Study Acceptance Criteria

Sample-Positive and negative control: variation coefficient must be <20%.

Variation Coefficient

VC=((sd/OD$_{average}$)×100)

p value (type 2 two-tailed t test) must be lower than 0.05%.

The Table below reports data related to free radical development. The data are reported, processed, in FIG. 5.

TABLE 10

| | FREE RADICAL DEVELOPMENT | | | | | | |
|---|---|---|---|---|---|---|---|
| | Composition of the invention | | | | | | |
| mg/ml | 0.5 mg/ml | 0.25 mg/ml | 0.125 mg/ml | 0.063 mg/ml | 0.03 mg/ml | Vit. C 0.05 mg/ml | Neg. Cntrl |
| T0 | 6311.67 | 6178 | 6072 | 7070 | 7237 | 5654 | 10315 |
| 20 MIN | 7026 | 6984 | 7993 | 9473 | 10308 | 5993 | 14015 |
| 40 MIN | 6643 | 6945 | 8228 | 10021 | 10758 | 5721 | 14248 |
| 60 MIN | 6192 | 6716 | 8543 | 9582 | 10140 | 5240 | 13120 |
| 80 MIN | 5952 | 6813 | 8861 | 9797 | 10173 | 4802 | 12789 |
| 100 MIN | 5534 | 6643 | 8857 | 9649 | 10181 | 4937 | 12600 |

The data reported in the table show that, at 0.5 mg/ml and 0.25 mg/ml dilutions, the values obtained with the composition of the invention are comparable to those obtained with vitamin C.

The obtained data were then processed in terms of % of protection from free radicals exerted by analyzed substances.

The Table below reports data related to the results obtained. What reported in the table below was graphically processed in FIG. 6.

TABLE 11

Composition of the invention
% PROTECTION FROM FREE RADICALS

| mg/ml | 0.5 mg/ml | 0.25 mg/ml | 0.125 mg/ml | 0.063 mg/ml | 0.03 mg/ml | Vit. C 0.05 mg/ml |
|---|---|---|---|---|---|---|
| T0 | 39 | 40 | 41 | 31 | 30 | 45 |
| 20 MIN | 50 | 50 | 43 | 32 | 26 | 57 |
| 40 MIN | 53 | 51 | 42 | 30 | 24 | 60 |
| 60 MIN | 53 | 49 | 35 | 27 | 23 | 60 |
| 80 MIN | 55 | 48 | 32 | 25 | 22 | 63 |
| 100 MIN | 56 | 47 | 30 | 23 | 19 | 61 |

The data reported in the table show that, at 0.5 mg/ml and 0.25 mg/ml dilutions, the values obtained with the composition of the invention are comparable to those obtained with vitamin C.

The table below reports the statistical significance of obtained results.

TABLE 12

STATISTICAL SIGNIFICANCE (p Value)

Composition of the invention

| mg/ml | 0.5 mg/ml | 0.25 mg/ml | 0.125 mg/ml | 0.063 mg/ml | 0.03 mg/ml | Vit. C 0.05 mg/ml |
|---|---|---|---|---|---|---|
| T0 | 9.26E-11 | 1.72E-10 | 8.79E-11 | 8.61E-09 | 5.25E-09 | 7.10E-11 |
| 20 MIN | 1.92E-09 | 3.38E-09 | 3.04E-08 | 1.05E-06 | 4.93E-06 | 6.88E-10 |
| 40 MIN | 6.56E-10 | 1.41E-09 | 1.57E-08 | 1.27E-06 | 8.58E-06 | 2.04E-10 |
| 60 MIN | 3.23E-09 | 2.14E-08 | 4.76E-07 | 1.54E-05 | 7.96E-05 | 8.91E-10 |
| 80 MIN | 1.44E-06 | 6.42E-06 | 3.54E-04 | 3.12E-03 | 8.32E-03 | 2.62E-07 |
| 100 MIN | 4.43E-07 | 3.20E-06 | 3.22E-04 | 2.42E-03 | 8.19E-03 | 1.71E-07 |

As is apparent from the above Table, statistical analysis of obtained results confirmed that the test carried out fulfills all required acceptability criteria, therefore validating the data generated for examined substances.

Summing up the foregoing, the assays performed on samples of the composition of the invention in various embodiments as described above demonstrated that the composition has a good scavenger action, able to neutralize $H_2O_2$-induced free radicals (FR): the first dose analyzed (0.5 mg/ml) reduces FR formation of the 39-50-53-53-55 and 56%, respectively, after each exposure time. By virtue of this result, this dose may be deemed the most effective dose.

The second dose analyzed (0.25 mg/ml) reduces FR formation of the 40-50-51-49-48 and 47%, respectively, after each exposure time.

At the third dose (0.125 mg/ml), FR formation is reduced of the 41-43-42-35-32 and 30%, respectively, after each exposure time.

At the fourth dose (0.0625 mg/ml) FR formation is reduced of the 31-32-30-27-25 and 23%, respectively, after each exposure time.

The fifth dose (0.0313 mg/ml) significantly inhibits FR formation of the 30-26-24-23-22 and 19%, respectively, after each exposure time.

Ascorbic acid (0.05 mg/ml) has a scavenger action able to reduce FRs of the 45-57-60-60-63 and 61%, respectively, after the six times of exposure to stress.

Neutral Red Uptake vitality assay, performed on the plate not exposed to oxidative stress, highlighted no reduction of cell vitality such as to compromise the significance of the assay.

Accordingly, the composition of the invention, taking into account the high force of the stress applied, proved to be a good scavenging agent.

3. Assessment of Stability of the Composition of the Invention

The stability of the composition of the invention in fluid form (syrup, as per examples above, at 2) with regard to tannins was assessed by measuring the content of total tannins, expressed as pyrogallol, by means of spectrophotometric method described in European Pharmacopoeia (EP 9.2, 2.8.14) for agrimony.

As can be observed from data reported in the Table below, no changes in titer are observed in the space of six months, keeping the sample under extreme conditions, at 40° C. and 75% of relative humidity.

Vitamin C, in preparations that differed in formulation solely due to the presence of vitamin C in lieu of the tannins, did not exhibit stability beyond T0.

| | Tannins such as Pyrogallol | | |
|---|---|---|---|
| Check point | T0 | T3 months | T6 months |
| Accelerated stability (40° C., RH 75%) | 0.05 | 0.05 | 0.05 |

4. Barrier Effect Assay

For the barrier effect assay, two chambers physically separated by a semi-permeable membrane (0.4 µm pores) were used. Human fibroblast cells were seeded in the lower chamber, whereas the inflammatory agent LPS (purified *E.*

Coli lipopolysaccharide) was introduced into the upper chamber; on the semi-permeable membrane separating the two chambers a thin film of the composition as described in the present invention was stratified.

Induced inflammatory response was estimated through semi-quantitative dosage of Interleukin 6 (IL6) cytokine released in the culture medium of the lower chamber: barrier effect assessment was obtained by comparison with the positive control in which the two chambers were separated by the same type of semi-permeable membrane, free however from any barrier.

As to the threshold value above which it may be said that a substance causes a barrier effect in the assay reported herein, a value equal to 15% of inhibition as compared to the control was identified by the Inventors, during the setting up of the assay, on the basis of assays carried out on substances known to have a barrier effect.

Then, the barrier effect of the composition in the formulations at 2. above was evaluated.

The data reported in FIG. 3 show how the composition has a remarkable barrier effect.

The assessment assay was carried out as follows, through a method developed to simulate in vitro the protective action of substances and formulations which, when applied to the skin and mucous membranes in vivo, form an "insulating" film against environmental agents.

The model takes advantage of the principle whereby cells subjected to contact with an inflammatory agent produce and secrete pro-inflammatory mediators (cytokines) in the extracellular environment in an amount related to the degree of inflammation caused. The greater the amount of inflammatory agent reaching the cells, the greater the amount of cytokines released.

Two chambers were set up, physically separated by a semi-permeable membrane which allows the transit of sufficiently small-sized solutes.

In the lower chamber, consisting of a well containing plates for cell cultures, HuDe cells (no. BS PRC 41, purchased from the Istituto Zooprofilattico di Brescia, Italy) are grown, while the upper chamber, consisting of an insert for complex cell cultures (transwells) accommodates the inflammatory agent.

On the surface of the semi-permeable membrane of the insert separating the two chambers On the surface of the semi-permeable membrane of the insert separating the two chambers, before the introduction of the inflammatory agent in the upper chamber, a thin film of the sample being examined is stratified to assess any BE upon the free transit of the inflammatory agent.

Depending on the insulating capabilities of the sample, there will be had a decrease of the migration of the inflammatory agent from the upper chamber and, as a consequence, a lesser stimulation of the cells to produce cytokines. The extent of the inflammatory reaction is estimated through the semi-quantitative dosage of cytokines released in the culture medium of the lower chamber, in particular of interleukin 6 (IL-6).

As a control a similar experiment is used in which no sample is stratified on the membrane, thus making it possible to measure the effect of the inflammatory agent without any barrier in addition to the semi-permeable membrane.

Moreover, an internal control is used in which the cultured cells are pre-treated with the substance adapted to induce marker release and the sample is placed on the semi-permeable membrane in the absence of said substance, one or more measurements in time are thus performed of the quantity of marker in the culture medium of said internal control. In the internal control, the cells are therefore stimulated first with the inducing substance and then there has to be assessed whether the sample which may pass the membrane and go into the cells pushed by the medium above has any effect in decreasing the release of the marker not related to the barrier effect. For instance, when an inflammatory agent is used as the inducing substance, the internal control makes it possible to understand if the reduction in the concentration of cytokines in the culture medium is due to the barrier effect or if the sample that may pass into the cells pushed by the medium above has any effect in reducing the inflammatory response independently of the barrier effect.

The barrier effect (BE) is expressed as a percentage of the reduction of the release of IL-6 and is calculated through comparison with the positive control in which the two chambers are separated by the same type of semi-permeable membrane without the barrier created by the sample.

4.1 Preparation of the Cell Culture

For each assayed sample (as per 2. above), HuDe line cells were seeded in the wells of a cell culture plate, one for the barrier assay (T.B.) (BA) and another one for the internal control at a density of 40,000 cells/ml in MEM medium supplemented with 10% bovine serum (FBS); 1 ml of cell suspension per well.

The cells were treated with the SAMPLE (CAM), with the POSITIVE CONTROL (C+) (inflammatory agent without sample), and with the NEGATIVE CONTROL (C−) (medium only) and each assay was carried out in triplicate.

The plates were incubated at 37° C., overnight (22-24 hours).

4.2 Preparation of Inserts for Complex Cell Cultures

Cell Culture Inserts (Becton Dickinson) for complex cell cultures were placed on other plates, and on each of them a fixed amount of collagen of 0.1 mg/ml was supplied. The plates were incubated at 37° C., overnight (22-24 hours).

In order to proceed with the experiment, a confluency not lower than 95% is expected.

From the two plates (BA and IC) with the inserts the collagen was removed, and the inserts were left under the flow of the hood for the time required to let them dry completely (10÷15 minutes).

4.3 Barrier Assays (BA)

The steps described below were carried out in the culture plate for the BA.

Setting Up of the Sample Layer in the BA:

On the semi-permeable membrane of the sample, 100 µl of a composition based on 0.5% alginate were inoculated and allowed to stratify for 20 minutes, while in the C+ and C− inserts nothing was added. Once the 20 minutes had elapsed, excess sample was eliminated, and the membranes washed with PBS according to procedures specified by the protocol.

Addition of LPS (Inflammatory Agent) to BA Inserts

Once the sample layer had dried, as per example at 2. above, in the first three CAM inserts and in the three C+ ones, 300 µl of the LPS (membrane lipopolysaccharide) solution were inoculated at the concentration of 1 µg/ml, while in the remaining three of the C− 300 µl of MEM medium with 5% FBS were added. The inserts were inserted in their respective wells with the cells and the plates were incubated for 1 h at 37° C. and under an atmosphere enriched with 5% $CO_2$ overnight (22-24 hours).

Once completed the 1 h incubation, the inserts were removed and discarded, and the plates were incubated again overnight (22-24 hours).

4.4 Internal Control (IC) Assay

The internal control assay was carried out concomitantly with the BA.

Exposure of IC Cells to LPS:

Once dried, in the first six inserts of IC, three for the sample to be analyzed, CAM, and three for the C+, 300 μl of the LPS solution were inoculated, while in the remaining three of the C− 300 μl of the medium were added.

The inserts with LPS and MEM were then inserted in the wells with IC cells and all incubated for 1 h.

LPS Removal and IC Membrane Drying:

Once completed the 1 h incubation, the inserts were removed from the wells with the cells and transferred to the empty plate, while the plate with the cells was placed in an incubator.

The LPS solution still present was removed from the inserts, the latter were subjected to a rapid wash with ultrapure sterile water and allowed to dry.

Arrangement of Sample Layer in the IC:

On the semi-permeable membrane of the three inserts for the sample, 100 μl of a composition based on 0.5% alginate were inoculated and allowed to stratify for 20 minutes, while in the C+ and C− inserts nothing was added. Once the 20 minutes had elapsed, the excess sample was eliminated, and the membranes were washed with PBS according to procedures specified by the protocol.

Addition of LPS to IC Inserts

Once the inserts with the sample were ready, 300 μl of medium were added to all inserts (CAM, C+, C−). The inserts were inserted in their respective wells with the cells and the plates incubated for 1 h at 37° C.

Once completed the 1 h incubation, the inserts were removed and discarded, and the plates incubated again overnight (22-24 hours).

4.5 Supernatant Collection and Enzyme Immunoassay

Once the 22-24 hours had elapsed, the supernatants were collected from the BA and the IC plates for performing the ELISA assay and the semi-quantitative dosage of IL-6.

Barrier Effect (BE) Assessment

The BE of a substance or compound is expressed as % reduction in the release of IL-6 cytokine by cells exposed to LPS wherein the sample has been assayed relative to the positive control (C+) wherein the cells have only been exposed to LPS.

BE=% reduction in release of IL-6 cytokine=100−[(pg/μL cytokine released from sample/pg/μL cytokine released from C+)×100]

As can be seen from the results in FIGS. 1-4, the composition of the invention has excellent mucoadhesive properties and a high barrier effect.

Apparently, therefore, beside free radical scavenger activity and stability over time, the composition also has barrier effect and high mucoadhesive properties.

5. Preparation of Fractions

1. Example of Preparation of Polysaccharide (Mucilage) Fraction of Marshmallow

Dried and crumbled marshmallow root is subjected to extraction by water, in a static extractor by percolate digestion, with the plant immersed in solvent and the solvent recycled bottom-to-top by a mechanical pump.

The drug-solvent ratio (DSR) is equal to 1:10, extraction temperature is of 90° C., extraction length is 12 hours. From the resulting mixture, the insoluble residue is separated from the soluble fraction by static decanting and subsequently by filtration on paper filter. The resulting solution is concentrated by ethanol evaporation, by use of a vacuum concentration system. Upon reaching a degree of concentration of 10:1, concentration is discontinued, and drying is completed by lyophilization or spray drying. The lyophilized material constitutes the fraction of interest (DER 4-10:1).

2. Example of Preparation of Polysaccharide Fraction of Plantain

Dried and crumbled plantain leaves are subjected to extraction by ethanol 50% (ethanol:water 50:50 v/v), in a static extractor by percolate digestion, with the plant immersed in solvent and the solvent recycled bottom-to-top by a mechanical pump. The drug-solvent ratio (DSR) is equal to 1:10, extraction temperature is of 50° C., extraction length is 6-8 hours. From the resulting mixture, the insoluble residue is separated from the soluble fraction by static decanting and subsequently by filtration on paper filter. The resulting solution is concentrated by ethanol evaporation, by use of a vacuum concentration system. Upon reaching a degree of concentration of 10:1, concentration is discontinued, and drying is completed by lyophilization or spray drying. The lyophilized material constitutes the fraction of interest (DER 4-10:1).

3. Example of Preparation of Polyphenolic Fraction of Agrimony

Dried and crumbled agrimony tops are subjected to extraction by water, in a static extractor by percolate digestion, with the plant immersed in solvent and the solvent recycled bottom-to-top by a mechanical pump.

The drug-solvent ratio (DSR) is equal to 1:8, extraction temperature is of 90° C., extraction length is 12 hours. From the resulting mixture, the insoluble residue is separated by static decanting and subsequently by filtration on paper filter. From the resulting mixture, the insoluble residue is separated from the soluble fraction by static decanting and subsequently by filtration on paper filter. The resulting solution is concentrated by ethanol evaporation, by use of a vacuum concentration system. Upon reaching a degree of concentration of 10:1, concentration is discontinued, and drying is completed by lyophilization or spray drying. The lyophilized material constitutes the fraction of interest (DER 4-10:1).

The invention claimed is:

1. A composition comprising 0.1-1% (w/v) polysaccharide fraction of plantain leaves, 0.1-1% (w/v) polysaccharide fraction of marshmallow, 0.1-1% (w/v) polyphenolic fraction of agrimony, 40-60% (w/v) brown sugar, 20-30% (w/v) honey, and 10-40% (w/v) water.

2. The composition according to claim 1, wherein said polysaccharide fraction of plantain comprises polysaccharides having a molecular weight higher than 20000 Daltons.

3. The composition according to claim 1, wherein said polysaccharide fraction of marshmallow comprises polysaccharides having a molecular weight higher than 20000 Daltons.

4. The composition according to claim 1, wherein further comprising excipients selected from natural flavorings, preservatives, and thickening agents.

5. The composition according to claim 4, wherein said one or more natural flavorings, preservatives, thickening agents are selected from lemon juice, blackberry juice, natural orange flavor, natural lemon flavor, natural myrtle flavor, and xanthan gum.

6. The composition according to claim 1, which is in the form of a tablet, pill, granules, powder, syrup, elixir, hard gelatin, soft gelatin, suspension, spray, emulsion, or solution.

7. The composition according to claim 1, characterized in that it has a percentage of mucoadhesion, measured with a lectin binding inhibition of between 85% and 50% when not diluted or diluted up to a maximum of 1:5.

8. A method of treating dry cough, productive cough, cough associated with upper respiratory tract infections (URTI), or cough resulting from post-nasal drip comprising administering a therapeutically effective amount of the composition of claim 1 to a subject in need thereof.

* * * * *